(12) United States Patent
Bondar (10) Patent No.: US 8,685,336 B2
(45) Date of Patent: Apr. 1, 2014

(54) SYSTEM AND METHOD FOR RECYCLING STERILANT GAS

(75) Inventor: Douglas E. Bondar, Martinez, GA (US)

(73) Assignee: Covidien LP, Mansfield, MA (US)

( * ) Notice: Subject to any disclaimer, the term of this patent is extended or adjusted under 35 U.S.C. 154(b) by 552 days.

(21) Appl. No.: 12/637,064

(22) Filed: Dec. 14, 2009

(65) Prior Publication Data

US 2010/0092344 A1  Apr. 15, 2010

Related U.S. Application Data

(62) Division of application No. 11/541,358, filed on Sep. 29, 2006, now Pat. No. 7,666,369.

(51) Int. Cl.
  *A61L 2/20* (2006.01)

(52) U.S. Cl.
  USPC ............................. 422/292; 422/31; 422/295

(58) Field of Classification Search
  USPC ........................................ 422/31, 292, 295
  See application file for complete search history.

(56) References Cited

U.S. PATENT DOCUMENTS

| | | | |
|---|---|---|---|
| 251,925 A | 1/1882 | Nietscke | |
| 867,831 A | 10/1907 | Nathan | |
| 1,126,430 A | 1/1915 | Elliott | |
| 1,675,123 A | 6/1928 | Metzger et al. | |
| 1,900,717 A | 3/1933 | Kilbourne | |
| 2,131,134 A | 9/1938 | Baer et al. | |
| 2,253,287 A | 8/1941 | Davis et al. | |
| 2,465,853 A | 3/1949 | Dalton., Jr. | |
| 3,097,916 A | 7/1963 | Dawson et al. | |
| 3,238,096 A | 3/1966 | Kaye | |
| 3,341,280 A | 9/1967 | Eolkin | |
| 3,372,980 A | 3/1968 | Satas | |
| 3,495,932 A | 2/1970 | Tuma | |
| 3,549,312 A | 12/1970 | Ernst | |
| 3,600,127 A | 8/1971 | Kercluk et al. | |
| 3,758,257 A | 9/1973 | Dastur | |
| 3,767,362 A | 10/1973 | Griffin et al. | |
| 3,893,843 A | 7/1975 | Fry et al. | |
| 3,897,210 A | 7/1975 | Gruber et al. | |
| 3,948,621 A | 4/1976 | Cocuzza et al. | |
| 3,963,438 A | 6/1976 | Banez | |
| 3,964,980 A | 6/1976 | Ozero | |
| 3,968,276 A | 7/1976 | Allen | |
| 3,989,461 A | 11/1976 | Skocypec et al. | |
| 4,028,070 A | 6/1977 | Uchii et al. | |
| 4,033,617 A | 7/1977 | Cocuzza et al. | |

(Continued)

FOREIGN PATENT DOCUMENTS

| | | |
|---|---|---|
| EP | 0 583 828 | 2/1994 |
| EP | 0 640 376 | 3/1995 |
| EP | 0 705 826 | 4/1996 |
| JP | 411145531 | 5/1999 |

*Primary Examiner* — Sean E Conley (57) ABSTRACT

A system for recovery and reutilization of sterilant gas mixture from a sterilizer chamber includes a storage tank in gaseous communication with a sterilizer chamber via a gas recovery assembly, wherein after sterilization the gas recovery assembly evacuates the sterilant gas mixture to the storage recovery tank. The system also includes an inert purge gas supply adapted to supply a purge gas to the sterilizer chamber after the sterilant gas mixture is withdrawn to the storage recovery tank, wherein the gas recovery assembly evacuates an additional portion of the purge gas from the sterilizer chamber to the storage tank to enrich the gas mixture for later reutilization in subsequent sterilization cycles.

19 Claims, 4 Drawing Sheets

PROCESS SCHEMATIC
Recovery of Sterilant Gas Using Tandem
100% EtO Sterilizers

(56) References Cited

U.S. PATENT DOCUMENTS

| | | | |
|---|---|---|---|
| 4,081,574 A * | 3/1978 | Hawkins et al. ............. 427/237 |
| 4,130,393 A | 12/1978 | Fox |
| 4,249,917 A | 2/1981 | Tarancon |
| 4,301,113 A | 11/1981 | Alguire et al. |
| 4,337,223 A | 6/1982 | Kaye |
| 4,343,765 A | 8/1982 | Elston et al. |
| 4,366,125 A | 12/1982 | Kodera et al. |
| 4,370,301 A | 1/1983 | Doi et al. |
| 4,396,582 A | 8/1983 | Kodera |
| 4,430,306 A | 2/1984 | Namba et al. |
| 4,447,399 A | 5/1984 | Runnells et al. |
| 4,474,734 A | 10/1984 | Cooper |
| 4,517,159 A | 5/1985 | Karlson |
| 4,555,251 A | 11/1985 | Jonsson et al. |
| 4,576,918 A | 3/1986 | Yeung |
| 4,591,485 A | 5/1986 | Olsen et al. |
| 4,637,916 A | 1/1987 | Hennebert et al. |
| 4,639,257 A | 1/1987 | Duckett et al. |
| 4,707,334 A | 11/1987 | Gerhard |
| 4,812,292 A | 3/1989 | Joslyn |
| 4,822,563 A | 4/1989 | Joslyn |
| 4,875,909 A | 10/1989 | Kakimoto et al. |
| 4,888,155 A | 12/1989 | Posey et al. |
| 4,902,493 A | 2/1990 | Walles et al. |
| 4,954,315 A | 9/1990 | Brahmbhatt |
| 4,966,755 A | 10/1990 | Smith |
| 4,975,245 A | 12/1990 | Archer et al. |
| 4,992,247 A | 2/1991 | Foti |
| 5,114,671 A | 5/1992 | Olanders |
| 5,120,512 A | 6/1992 | Masuda |
| 5,128,101 A | 7/1992 | Boynton |
| 5,149,500 A | 9/1992 | Brahmbhatt et al. |
| 5,152,968 A | 10/1992 | Foti et al. |
| 5,209,902 A | 5/1993 | Matthews et al. |
| 5,223,217 A | 6/1993 | Frizziero |
| 5,229,071 A | 7/1993 | Meo, III |
| 5,246,663 A | 9/1993 | Ohama et al. |
| 5,261,250 A | 11/1993 | Missimer |
| 5,266,275 A | 11/1993 | Faddis |
| 5,268,144 A | 12/1993 | Heilmann et al. |
| 5,283,035 A | 2/1994 | Karthaus et al. |
| 5,286,447 A | 2/1994 | Fannin et al. |
| 5,340,538 A | 8/1994 | Zaicow et al. |
| 5,366,872 A | 11/1994 | Hird et al. |
| 5,368,815 A | 11/1994 | Kasting, Jr. et al. |
| 5,417,921 A | 5/1995 | Dove et al. |
| 5,424,034 A | 6/1995 | Hilmersson |
| 5,464,580 A | 11/1995 | Popescu et al. |
| 5,472,667 A | 12/1995 | Karthaus et al. |
| 5,474,789 A | 12/1995 | Hayami et al. |
| 5,505,908 A | 4/1996 | Nagji |
| 5,520,881 A | 5/1996 | Koestler et al. |
| 5,525,295 A | 6/1996 | Pflug et al. |
| 5,600,142 A | 2/1997 | Van Den Berg et al. |
| 5,698,011 A | 12/1997 | Chung et al. |
| 5,741,470 A | 4/1998 | Wenzler |
| 5,744,688 A | 4/1998 | Vance et al. |
| 5,792,422 A | 8/1998 | Lin et al. |
| 5,804,139 A | 9/1998 | Lin et al. |
| 5,824,239 A | 10/1998 | Jaquess |
| 5,830,409 A | 11/1998 | Childers et al. |
| 5,837,193 A | 11/1998 | Childers et al. |
| 5,843,374 A | 12/1998 | Sizer et al. |
| 5,868,997 A | 2/1999 | Wyman |
| 5,891,393 A | 4/1999 | Read et al. |
| 5,904,909 A | 5/1999 | Yates et al. |
| 5,922,277 A | 7/1999 | Donhoff et al. |
| 5,932,171 A | 8/1999 | Malchesky |
| 5,932,172 A | 8/1999 | Winks |
| 5,961,936 A | 10/1999 | Heredia |
| 5,993,739 A | 11/1999 | Lyon |
| 6,007,780 A | 12/1999 | Heredia |
| 6,019,940 A | 2/2000 | Klobucar et al. |
| 6,051,188 A | 4/2000 | Spickermann |
| 6,068,815 A | 5/2000 | Oberleitner et al. |
| 6,106,773 A | 8/2000 | Miekka et al. |
| 6,171,551 B1 | 1/2001 | Malchesky et al. |
| 6,187,266 B1 | 2/2001 | Lin et al. |
| 6,203,756 B1 | 3/2001 | Lin et al. |
| 6,207,460 B1 | 3/2001 | Kishkovich et al. |
| 6,235,240 B1 | 5/2001 | Heredia et al. |
| 6,290,906 B1 | 9/2001 | MacNeal |
| 6,331,272 B1 | 12/2001 | Sims |
| 6,379,616 B1 | 4/2002 | Sheiman |
| 6,403,359 B1 | 6/2002 | Purmal et al. |
| 6,432,357 B1 | 8/2002 | Richard et al. |
| 6,468,469 B2 | 10/2002 | Huth |
| 6,475,444 B1 | 11/2002 | Zimmermann et al. |
| 6,495,095 B1 | 12/2002 | Goeldner |
| 6,514,459 B1 | 2/2003 | Crisinel et al. |
| 6,517,775 B1 | 2/2003 | Wang et al. |
| 6,537,491 B1 | 3/2003 | Wang et al. |
| 6,541,260 B1 | 4/2003 | Pariseau et al. |
| 6,558,622 B1 | 5/2003 | Malchesky |
| 6,585,934 B1 | 7/2003 | Oberleitner et al. |
| 6,589,478 B1 | 7/2003 | Keim et al. |
| 6,596,232 B1 | 7/2003 | Lin et al. |
| 6,605,253 B1 | 8/2003 | Perkins |
| 6,617,100 B2 | 9/2003 | Purmal et al. |
| 6,638,476 B1 | 10/2003 | Elias et al. |
| 6,656,427 B2 | 12/2003 | Lin et al. |
| 6,656,472 B1 | 12/2003 | Chong et al. |
| 6,746,647 B2 | 6/2004 | Kohler et al. |
| 6,821,481 B1 | 11/2004 | Osajima et al. |
| 6,863,905 B1 | 3/2005 | Shanbrom |
| 7,008,591 B2 | 3/2006 | Kafesjian et al. |
| 7,153,471 B2 | 12/2006 | Weinberg et al. |
| 7,160,509 B2 | 1/2007 | Masaoka |
| 2002/0081228 A1 | 6/2002 | Hui et al. |
| 2003/0086820 A1 | 5/2003 | McDonnell et al. |
| 2005/0163655 A1 | 7/2005 | Lin et al. |
| 2007/0025897 A1 | 2/2007 | Rheingans et al. |
| 2007/0253865 A1 | 11/2007 | Tsutsui et al. |
| 2008/0014111 A1 | 1/2008 | Hedman |

\* cited by examiner

FIG. 1

PROCESS SCHEMATIC
100% Ethylene Oxide Sterilizer System with Sterilant Gas Recovery
Combined Function Circulation & Vacuum Booster Blower

PROCESS SCHEMATIC
Recovery of Sterilant Gas Using Triple 100% EtO Sterilizers

FIG. 4

SYSTEM AND METHOD FOR RECYCLING STERILANT GAS

CROSS-REFERENCE TO RELATED APPLICATION

The present application is a divisional application of U.S. patent application Ser. No. 11/541,358, now U.S. Pat. No. 7,666,369 B2, entitled "SYSTEM AND METHOD FOR RECYCLING STERILANT GAS" filed by Douglas E. Bondar on Sep. 29, 2006, the entire disclosure of which is hereby incorporated by reference herein.

BACKGROUND

1. Technical Field

The present disclosure relates to a system and method for recycling sterilant gas. In particular, the present disclosure is directed to recovery and reuse of high concentration flammable sterilant gas mixtures, wherein the sterilant gas mixture is in concentrations greater than 20% by volume to a near an undiluted state of 100% by volume.

2. Discussion of Related Art

Ethylene oxide ("ETO") is a sterilizing agent well known for its effectiveness at certain gas concentrations. The objects which are to be sterilized are placed in a hermitically sealed sterilization chamber and the ETO vapor is pumped into the chamber. ETO gas is extremely flammable even in the absence of air and is, therefore, used with extreme caution in high concentrations at low pressures for sterilization purposes. Presently, high concentration ETO gas is not recycled and is only used once, afterwards the gas is then discharged to an emission control device for destruction.

One method for reusing ETO gas involves the use of a low concentration mixture of ETO and an inert gas at higher process pressures. High process pressures (e.g., up to 4 atmospheres) allow an increase in the ETO gas concentration to an acceptable milligram per liter value for effective sterilization. Mixtures having ratios of ETO to inert gas of 10/90 and 20/80 are generally used. These mixtures contain sufficient ETO concentration to assure sterilization regardless of the material being sterilized under normal temperature and at above atmospheric pressure conditions. Relative non-flammability of diluted ETO and inert gas mixtures allows for recycling of these mixtures. However, these mixtures are not as effective as higher concentrations of ETO gas.

The concentration of ETO decreases with continual use during the sterilization process since ETO is consumed in reaction with bacteria, water vapor, alcohol and the like during the sterilization process. It is possible for the ETO gas concentration to be consumed to an unsatisfactory concentration for consistent sterilization effect. Therefore, low concentration gas mixtures require processing using higher pressure rated vessels, which are more expensive. This process also involves processing the gases at above atmospheric pressures and, therefore, carries the risk of fugitive and catastrophic leakage. Consequently, in the industry today, all large ETO sterilizer chambers are designed to operate using low pressure and high concentration ETO gas. Existing sterilizers in use in the industry are not rated for the higher pressures that are required to recycle low concentration ETO gas sterilants.

It is desirable to provide a system and method for recycling sterilant gas mixtures having near 100% concentration of ETO gas to obtain maximum sterilization effectiveness while minimizing the complexity of the process and the cost of the sterilization equipment. It is desirable to provide a system that can be retrofitted to existing sterilization facilities, by the utilization of the existing sterilization process equipment and avoiding the expenses that are associated with complete system replacement.

SUMMARY

The present disclosure relates to a system and method for recycling high concentration ethylene oxide ("ETO") gas mixtures used in industrial sterilization processes. The system includes a sterilizer chamber in gaseous communication with a storage tank and a gas recovery assembly (e.g., vacuum draw). The gas recovery assembly withdraws the ETO gas to the storage tank which is adapted to store the sterilant gas at a pressure lower than the atmospheric pressure to minimize flammability thereof and fugitive leakage from the system. The ETO gas is stored in the storage tank until the sterilization chamber is to be charged with the ETO gas. It is envisioned that the storage tank may be replaced with a second sterilization chamber to allow for in tandem sterilizations. A third or forth sterilization chamber may also be connected to the system to allow gas transfer of the ETO gas from one sterilization chamber to the next chamber, thereby continually utilizing recycled gas in each sterilizer charge.

According to one embodiment of the present disclosure, a system for recovery of sterilant gas from a sterilizer chamber is disclosed. The system requires the use of an initial sterilizer evacuation and dilution with an inert purge gas to eliminate the air from the sterilizer chamber. The system includes a storage tank in gaseous communication with a sterilizer chamber via a gas recovery assembly, wherein gas can be evacuated in either direction between the sterilizer chamber and the gas storage tank utilizing the recovery system. The system utilizes an inert purge gas to dilute the residual ETO gas remaining in the sterilizer chamber to a safe nonflammable concentration, after the sterilant gas is evacuated to the storage tank. The gas recovery assembly evacuates additional diluted gas from the sterilizer chamber to the storage tank to further increase the quantity of sterilant gas being recycled.

According to another embodiment of the present disclosure a method for recovery of sterilant gas from a sterilizer chamber is disclosed. The method includes the steps of: evacuating a sterilant gas after sterilization from a sterilizer chamber via a gas recovery assembly to a storage tank. An inert purge gas is added to the sterilizer chamber after the sterilant gas charge is withdrawn to the storage tank to reduce the flammability of the sterilant gas. Some of the purge gas is withdrawn from the sterilizer chamber and directed to the storage tank to be utilized in the enrichment of the gas mixture in the storage tank.

According to an embodiment of the present disclosure, a system for recovery of sterilant gas mixture from a sterilizer chamber is disclosed. The system includes a first sterilizer chamber in gaseous communication with a second sterilizer chamber via a gas recovery assembly. After sterilization of the first sterilizer chamber, the gas recovery assembly evacuates the sterilant gas mixture to the second sterilizer chamber, where the mixture enriched with 100% ETO to a predetermined gas concentration to sterilize objects in the second sterilizer chamber. The system also supplies an inert gas to the second sterilizer chamber after the sterilant gas mixture has been evacuated to the second sterilizer chamber, wherein the gas recovery assembly withdraws the purge gas from the first sterilizer chamber to the second sterilizer chamber to be utilized as additional replacement gas for the sterilant gas mixture in the second sterilizer chamber.

BRIEF DESCRIPTION OF THE DRAWINGS

Various embodiments of the present disclosure are described herein with reference to the drawings wherein.

DETAILED DESCRIPTION

Particular embodiments of the present disclosure are described herein below with reference to the accompanying drawings. In the following description, well-known functions or constructions are not described in detail to avoid obscuring the present disclosure in unnecessary detail.

Figure 1:
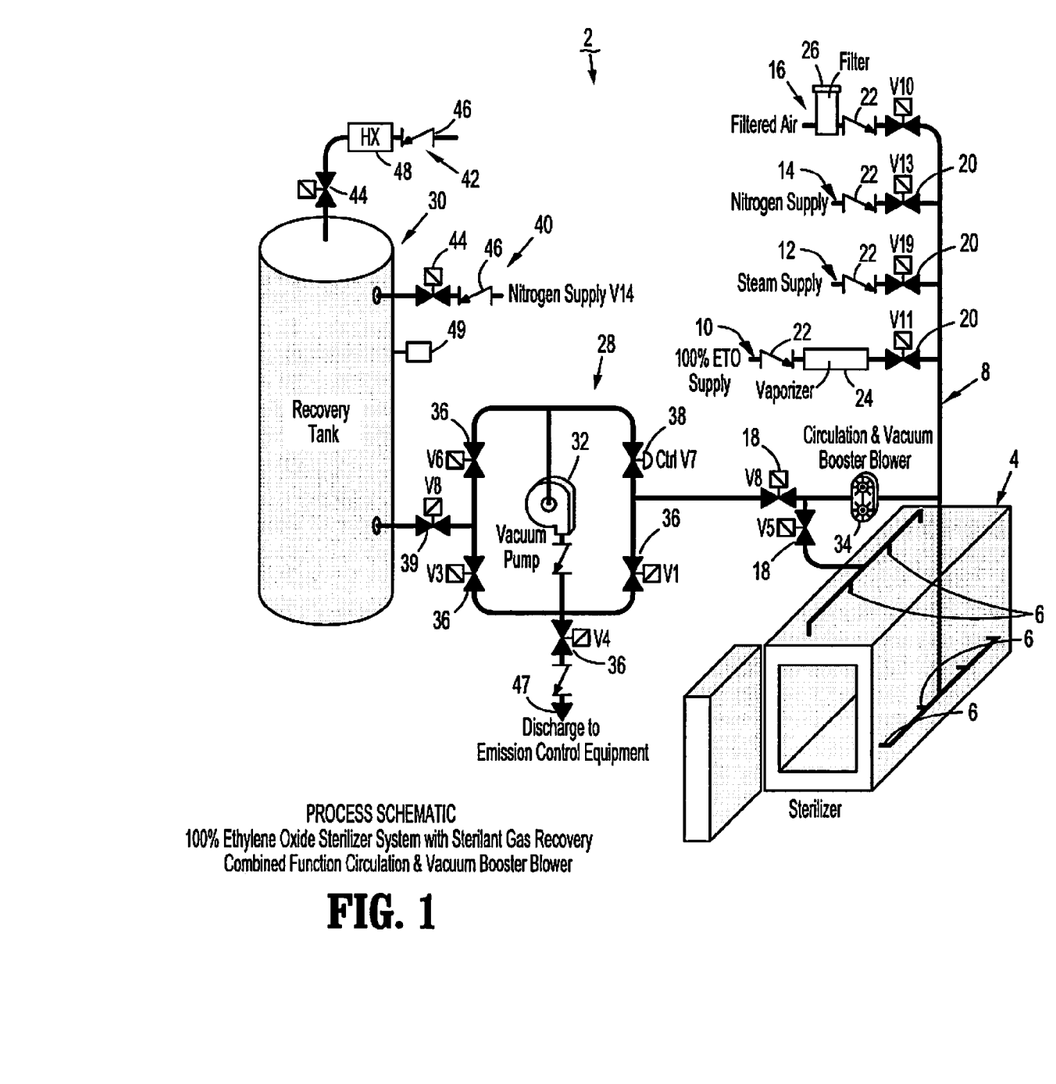
FIG. 1 is a schematic view of one embodiment of a sterilant gas recycling system according to the present disclosure.

Referring now to FIG. 1, a recycling system 2 in accordance with the principles of the present disclosure is illustrated. The recycling system 2 is adapted to recapture and reuse a sterilant gas, such as ethylene oxide ("ETO"). Those skilled in the art will appreciate that the present disclosure is not limited to recycling of ETO and that other suitable gases selected for their sterilization properties may be used.

The recycling system 2 includes a sterilizer chamber 4 which is configured to be hermetically sealed once objects in need of sterilization are placed therein to prevent gaseous flow between the sterilizer chamber 4 and the outside. The sterilizer chamber 4 includes one or more gas inlets 6 connected to a gas supply line 8. The gas supply line 8 includes an ETO supply 10, a steam supply 12, a purge gas supply 14, and a filtered air supply 16. The gas supply line 8 also includes pressure actuated shut-off valves 18 in communication with piping leading to the gas inlets 6. Each of the supplies 10, 12, 14 and 16 include a secondary pressure actuated shut-off valve 20 and a check valve 22 which allows for unidirectional flow of gasses into the sterilizer chamber 4.

The ETO supply 10 provides a direct source of ETO gas to the sterilizer chamber 4 for the initial supply of ETO gas prior to commencement of recycling process as well as for any refortification of the ETO gas. The ETO supply 10 includes a heat exchanger 24 that is used to convert (e.g., vaporize) the liquid 100% ETO from the supply drums (not explicitly shown) to vapor state. The steam supply 12 provides water steam in multi-stage sterilization processes. The purge gas supply 14 provides a purge gas (e.g., nitrogen, carbon dioxide, etc.) to the ETO gas within the sterilizer chamber 4 to decrease the flammability of the ETO gas and to purge any remnants of the ETO gas after the first vacuum draw as discussed in more detail below. The air supply 16 includes an air vent 26 and provides a supply of filtered air which is used to fill the sterilizer chamber 4 after the ETO gas has been withdrawn to return the sterilizer chamber 4 to normal atmospheric conditions.

The recycling system 2 also includes a gas recovery assembly 28 which is in gaseous communication with the sterilizer chamber 4 and a recovery storage tank 30. The gas recovery assembly 28 transfers the ETO gas from the sterilizer chamber 4 into the recovery tank 30. The gas recovery assembly 28 includes a vacuum pump 32 and a circulation blower 34. The pump 32 is connected to a plurality of pressure controlled shut off valves 36 which control the direction of the gas flow through the gas recovery assembly 28. In addition, the gas recovery assembly 28 includes a manual control valve 38 which allows to terminate gas flow therein (e.g., emergency situations). The circulation blower 34 can be configured to facilitate gas flow out of the sterilizer chamber 4 by functioning as a vacuum booster blower in series prior to the vacuum pump 32, to effect a deeper recovery vacuum from the sterilizer chamber, which will maximize the quantity of sterilant gas recovered.

Piping connecting the recovery tank 30 to the gas recovery assembly 28 includes a pressure controlled shut-off valve 39. The recovery tank 30 also includes a purge gas supply 40 and an ETO supply 42. Each of the supplies 40 and 42 include a pressure controlled shut-off valve 44 and a check valve 46. Further, the ETO supply 42 includes a heat exchanger 48 to vaporize liquid ETO. The purge and ETO gas supplies 40 and 42 provide the storage tank 30 with nitrogen and ETO gases respectively such that the ratio of the gases can be adjusted during the recycling process.

Since the sterilant gas being used is high concentration ETO gas, the sterilization is accomplished at approximately atmospheric pressure to minimize flammability of the gas. It is also envisioned that the sterilizer chamber 4 and the storage tank 30 as well as other components of the recycling system 2 are rated for operation with flammable gas mixtures. During operation, the ETO gas is mixed with the purge gas in desired concentrations in the recovery tank 30 through the purge and ETO gas supplies 40 and 42 to form a sterilant gas mixture. Once objects are loaded into the sterilizer chamber 4, the chamber 4 is evacuated to remove air. Purge gas is added to the sterilizer chamber 4 through the purge gas supply 14 and the sterilizer chamber 4 is again evacuated. This may be repeated a few times to ensure that all air is removed from the sterilizer chamber 4. Thereafter, the sterilant gas mixture is pumped into the sterilizer chamber 4 along with pure ETO gas and purge gas to achieve the desired gas ratio. The circulation blower 34 is activated to mix the gases within the sterilant chamber 4.

After the sterilant gas mixture has been in the sterilizer chamber 4 for a sufficient amount of time to sterilize its contents, the vacuum pump 32 evacuates the sterilizer chamber 4 and transfers to gas mixture back to the recovery tank 30. As the sterilant gas mixture is transferred, the pressure within the sterilizer chamber 4 is lowered to substantially vacuum conditions given structural limitations of the sterilizer chamber 4 and capacity of the vacuum pump 32. The recovery tank 30 has a larger volume than the sterilizer chamber 4 (e.g., 110% of the volume of the sterilizer chamber 4) such that the pressure of transferred ETO gas therein is lower than the pressure of the gas within the sterilizer chamber 4 (i.e., atmospheric pressure). Since throughout the sterilization process all gases are stored and handled at pressures which are less than atmospheric, the environmental risk of fugitive gas leakage is drastically reduced.

After the recovery vacuum draw has been completed, the pressure in the sterilizer chamber 4 is increased to approximately 3 PSI by adding a purge gas (e.g., nitrogen gas) from the purge gas supply 14. A second stage recovery vacuum draw is performed to recover gas from the sterilizer chamber 4 until the recovery tank 30 has achieved the target pressure capacity, thereby mixing the ETO gas with the purge gas. The sterilizer chamber 4 is then pressurized to atmospheric pressure using purge gas from the purge gas supply 14 or air from the filtered air supply 16, if the contents of the sterilizer chamber 4 are non-flammable. Thereafter, subsequent vacuum draws via the vacuum pump 32 are discharged to standard emission control equipment (not specifically shown) through a discharge vent 47.

The air is purged by the initial vacuum draws and displaced with inert dilution gas so that the percentage of air in the gas mixture does not exceed 20%. If the sum of the ETO percentage and the inert dilution gas is less than 80%, then gas is vented off to the emission control device and replaced with pure 100% dilution gas.

The ETO gas mixture is stored in the recovery tank 30 at atmospheric pressure and is transferred back to the sterilizer chamber 4 during the next sterilization cycle via the vacuum pump 32. Prior to starting a sterilization process cycle, the sterilant gas mixture in the recovery tank is sampled and analyzed using a process gas analyzer 49. The analyzer 49 can be installed at a port of a pressure vessel (e.g., recovery tank 30, sterilizer chamber 4, etc.) or can be connected to multiple vessels through a valve network of tubing. The analyzer 49 can utilize gas chromatography, or infrared spectral analysis, to obtain reliable measurements of the ETO gas and the purge gas amounts. It is desirable to know the percentages of the gas components to ensure process safety. More specifically, concentration of gas components allows for calculation of the flammability of the process gas mixture and sterilization effect on the objects in the sterilizer chamber 4.

The sterilization process according to the present disclosure is configured to operate via variety of validated ETO gas concentrations. The gas concentration is measured in the sterilizer chamber 4 during the sterilization gas exposure dwell. The pressure is then adjusted according to the ideal gas law to control the gas density that the objects being sterilized are exposed. Additional ETO gas is provided through the ETO gas supply 10 if the gas mixture within the sterilizer chamber 4 needs to be refortified. It is envisioned that ETO gas recovery is about 85% of the original charge, wherein about 15% of the ETO gas is lost due to product absorption, glycol conversion, vacuum pull down limitations, etc.

Figure 2:
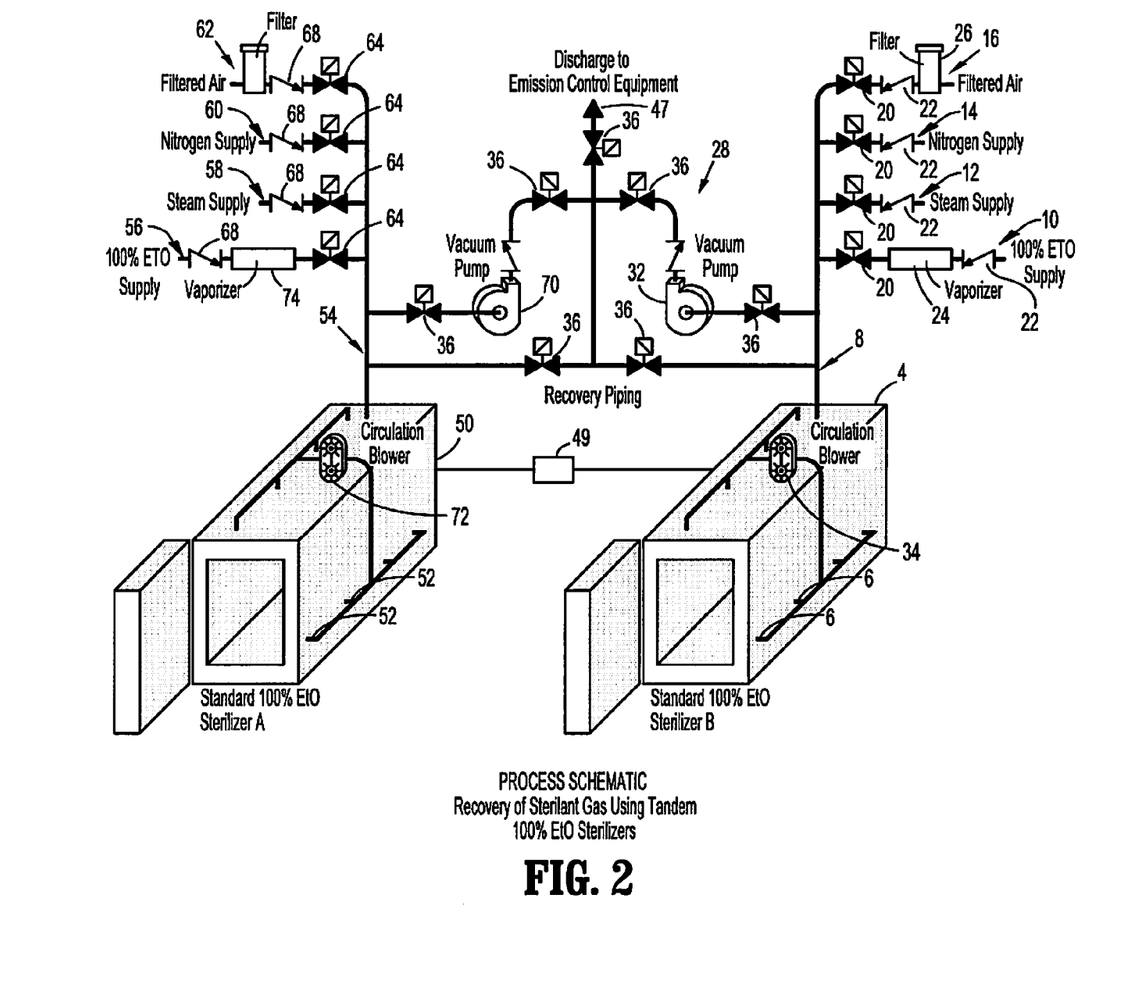
FIG. 2 is a schematic view of another embodiment of a sterilant gas recycling system according to the present disclosure.

Referring to FIG. 2, another embodiment of the recycling system 2 is illustrated, wherein the storage tank 30 is replaced with a second sterilizer chamber 50 which is in gaseous communication with the first sterilizer chamber 4. The sterilizer chamber 50 is configured to be hermetically sealed and includes similar components as the sterilizer chamber 4. In particular, the sterilizer chamber 50 includes one or more gas inlets 52 connected to a gas supply line 54 which includes an ETO gas supply 56, a steam supply 58, a purge gas supply 60, and a filtered air supply 62. Each of the supplies 56, 58, 60 and 62 include a secondary pressure actuated shut-off valve 64 and a check valve 68 which allows for unidirectional flow of gasses into the sterilizer chamber 50.

The gas recovery assembly 28 transfers the ETO gas between the sterilizer chamber 4 and the sterilizer chamber 50. The gas recovery assembly 28 includes the vacuum pump 32, the circulation blower 34, a second vacuum pump 70 and the circulation blower 72. The pumps 32 and 70 are connected to a plurality of pressure controlled shut off valves 36 which control the direction of the gas flow through the gas recovery assembly 28. The circulation blowers 34 and 72 are configured to facilitate gas flow between the sterilizer chambers 4 and 50.

During operation, the ETO gas is mixed with the purge gas in desired concentrations in the sterilizer chamber 50 through the ETO and purge gas supplies 56 and 60 to form a sterilant gas mixture. Once objects are loaded into the sterilizer chamber 4, one or more vacuum draws are performed using purge gas to fill the sterilizer chamber 4. Thereafter, the sterilant gas mixture is pumped into the sterilizer chamber 4 along with pure ETO gas and purge gas to achieve the desired gas ratio. The circulation blower 34 is activated to mix the gases within the sterilant chamber 4.

After the sterilant gas mixture has been in the sterilizer chamber 4 for a sufficient amount of time to sterilize its contents, the vacuum pump 32 evacuates the sterilizer chamber 4 and transfers to gas mixture back to the sterilizer chamber 50. As the ETO gas is transferred, the pressure within the sterilizer chamber 4 is lowered to substantially vacuum conditions given structural limitations of the sterilizer chamber 4 and capacity of the vacuum pump 32. The sterilizer chamber 50 has a substantially same volume as the sterilizer chamber 4 such that the pressure of transferred ETO gas therein is the same as the pressure of the gas within the sterilizer chamber 4 (i.e., atmospheric pressure).

After the recovery vacuum draw has been completed, the pressure in the sterilizer chamber 4 is increased to approximately 3 PSI by adding a purge gas (e.g., nitrogen gas) from the purge gas supply 14. A second stage recovery vacuum draw is performed to recover gas from the sterilizer chamber 4 until the sterilizer chamber 50 has achieved the target pressure capacity, thereby mixing the ETO gas with the purge gas. The sterilizer chamber 4 is then pressurized to atmospheric pressure using purge gas from the purge gas supply 14 or air from the filtered air supply 16, if the contents of the sterilizer chamber 4 are non-flammable. Thereafter, subsequent vacuum draws via the vacuum pump 32 are discharged to standard emission control equipment (not specifically shown) through the discharge vent 47.

Additional ETO gas is provided to the sterilizer chamber 50 through the ETO gas supply 56 if the gas mixture within the sterilizer chamber 50 needs to be refortified. A heat exchanger 74 vaporizes liquid ETO into gaseous state. The recovered ETO gas mixture is kept within the sterilizer chamber 50 at atmospheric pressure and is transferred back to the sterilizer chamber 4 during the next sterilization cycle once the sterilizer chamber 4 is prepared for another sterilization load.

Figure 3:
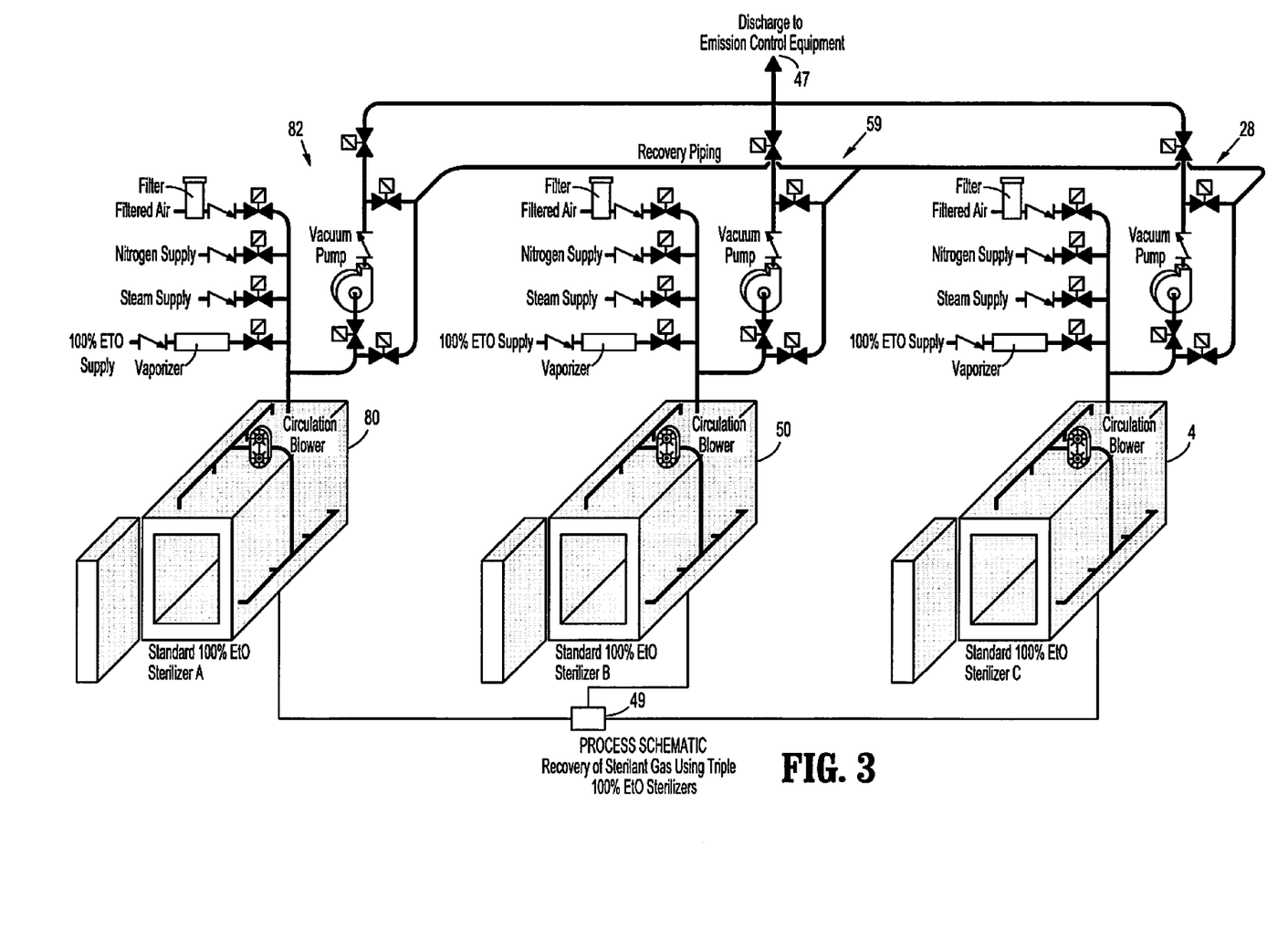
FIG. 3 is a schematic view of another embodiment of a sterilant gas recycling system according to the present disclosure.

Those skilled in the art will appreciate that multiple sterilization chambers may be connected to each other to facilitate in tandem sterilization, thereby recycling the ETO gas by transferring the gas from one chamber or storage tank to another. FIG. 3 shows a further modification of three sterilizer chambers 4, 50 and 80 connected in tandem as a single recovery system. The sterilant gas mixture is transferred from one sterilizer chamber to the next during the sterilization process. The sterilizer chamber 80 is connected to a recovery system 80 which is in gaseous communication with a recovery system 59 of the sterilizer chamber 50 and the recovery system 28 of the sterilizer chamber 4. Those skilled in the art will readily appreciate that the recovery systems 4, 59 and 80 and the sterilizer chambers 4, 50 and 80 include similar components as discussed above with embodiments shown in FIGS. 1-2 (e.g., vacuum pumps, filtered air, nitrogen, steam and ETO gas supplies, etc.). This arrangement is desirable when objects to be sterilized need to spend extended periods of time in the sterilizer chambers, e.g., for humidification and temperature warming prior to gas exposure, extended product off-gassing time in the chamber, etc. The use of three or four sterilizer chambers operating in a staggered manner may also be desirable to sterilize certain dense types of product.

Figure 4:
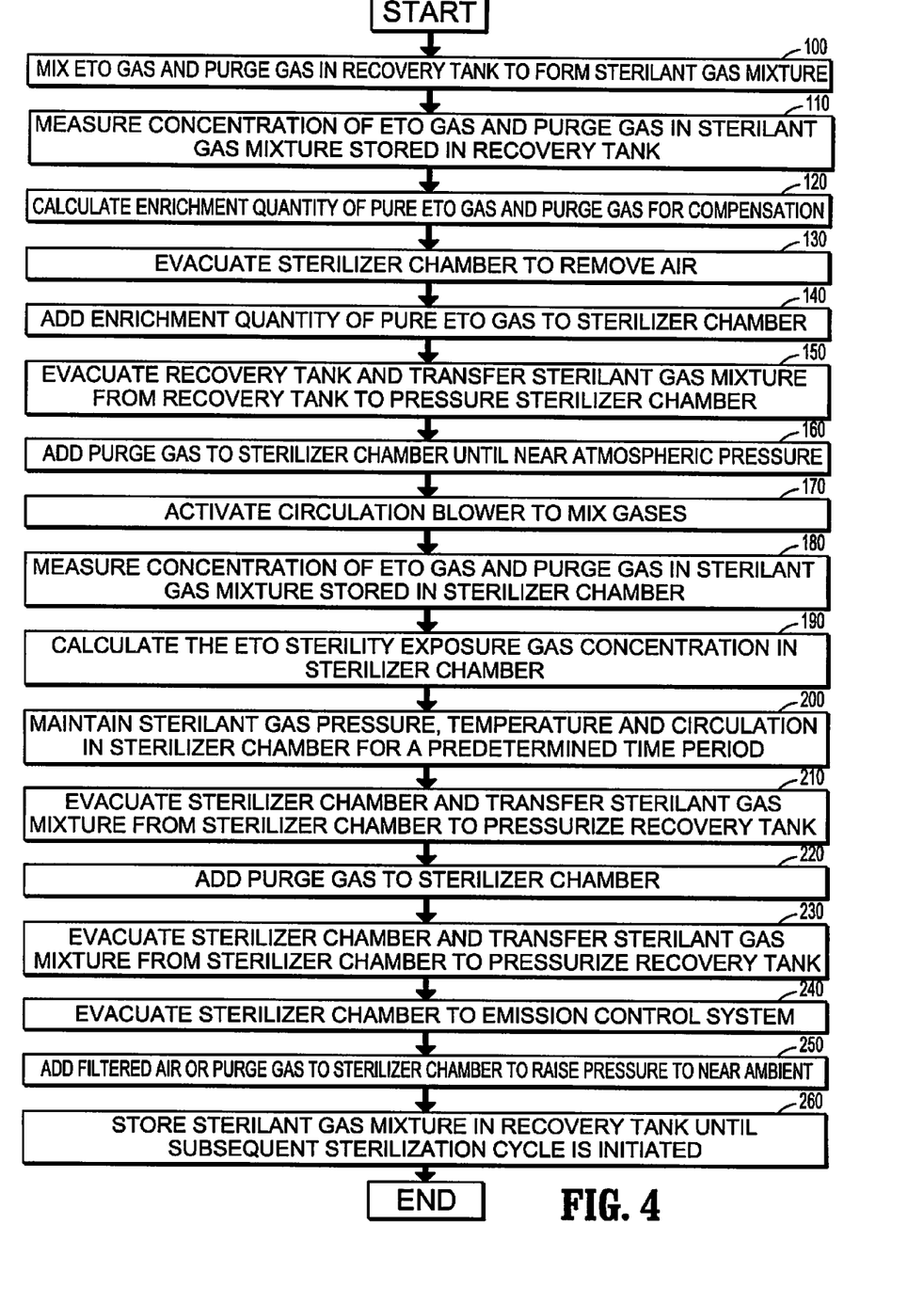
FIG. 4 is a flow diagram of a method for recycling sterilant gas according to the present disclosure.

FIG. 4 shows a flow chart of a method for recycling sterilant gas according to the present disclosure. In step 100, ETO gas and purge gas are mixed in desired proportions to form a sterilant gas mixture in the recovery tank 30 or a sterilizer chamber, if an in tandem system is being used. In step 110, concentration of the ETO and purge gases in the sterilant gas mixture is measured using the gas analyzer 49 to ensure a safe and effective sterilant gas composition. In step 120, enrichment quantities for ETO and purge gases are calculated to ensure that the concentration of ETO gas and pressure within the sterilizer chamber 4 is at a predetermined set point. In step 130, the sterilizer chamber 4 is evacuated and purged of air using one or more vacuum draws and a dilution via purge gas. In step 140, undiluted ETO gas is added into the sterilizer chamber 4 to provide an initial charge of gas into the sterilizer based on the calculations of step 120.

In step 150, the sterilant gas mixture in the recovery tank 30 is evacuated into the sterilizer chamber 4. In step 160, the purge gas is added to the sterilizer chamber 4 to raise the chamber pressure to near atmospheric pressure to minimize the risk of air leaking into the chamber based on the calculations of step 120. In step 170, the circulation blower 34 is activated to mix the gases added into the sterilization chamber. In step 180, concentration of ETO and purge gases in the sterilant chamber 4 is measured. In step 190, ETO gas sterility exposure gas concentration (e.g., milligrams per liter) is calculated. In step 200, the gas mixture is circulated and is maintained at a predetermined temperature and pressure within the sterilizer chamber 4. The sterilant gas mixture is kept in the sterilizer chamber 4 for a sufficient amount of time, at validated temperature and predetermined concentration parameters to sterilize its contents. In step 210, the sterilizer chamber 4 is evacuated to transfer the sterilant gas mixture back to the recovery tank 30 to pressurize the recovery tank 30 at or near the atmospheric pressure. After the recovery vacuum draw has been completed, in step 220, purge gas (e.g., nitrogen gas) from the purge gas supply 14 is added to the sterilizer chamber 4. This increases the pressure in the sterilizer chamber 4 to approximately 3 PSI. In step 230, a second stage recovery vacuum draw is performed to recover gas from the sterilizer chamber 4 until the sterilizer chamber 50 or the storage tank 30 has achieved the target pressure capacity. In step 240, once the recovery tank 30 is at the desired pressure set point, the contents of the sterilizer chamber 4 are evacuated to the emission control system. In step 250, the sterilizer chamber 4 is pressurized to atmospheric pressure using purge gas from the purge gas supply 14 or air from the filtered air supply 16. Optionally, subsequent vacuum draws are discharged to standard emission control equipment through the discharge vent 47. In step 260, the mixture of ETO gas and the purge gas is stored in the recovery tank 30 or the sterilization chamber 50. The recovered ETO gas mixture is kept within the recovery tank 30 or the sterilizer chamber 50 at near atmospheric pressure and is transferred back to the sterilizer chamber 4 during the next sterilization cycle once the sterilizer chamber 4 is prepared for another sterilization load.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for recovery of a sterilant gas mixture comprising:
    a sterilant gas mixture supply including a sterilant gas mixture comprising ethylene oxide;
    a first sterilizer chamber in gaseous communication with a second sterilizer chamber via a gas recovery assembly, wherein the first and second sterilizer chambers are coupled to the sterilant gas mixture supply and are configured to house at least one object for sterilization, and wherein the gas recovery assembly is configured to withdraw the sterilant gas mixture from the first sterilizer assembly after sterilization of the at least one object and introduce the gas sterilant mixture into the second sterilizer chamber; and
    a purge gas supply adapted to supply a purge gas to the first sterilizer chamber after the sterilant gas mixture is introduced into the second sterilizer chamber, wherein the gas recovery assembly includes a vacuum pump and a circulation blower adapted to withdraw the purge gas from the first sterilizer chamber to the second sterilizer chamber to form a combined mixture of the sterilant gas mixture and the purge gas.

2. A system according to claim 1, wherein the purge gas is an inert gas.

3. A system according to claim 1, wherein the second sterilizer chamber is evacuated prior to the sterilant gas mixture being withdrawn from the first sterilizer chamber.

4. A system according to claim 1, wherein the gas recovery assembly is configured to pressurize the first sterilizer chamber at the atmospheric pressure after the purge gas is withdrawn from the first sterilizer chamber and introduces into the second sterilizer chamber.

5. A system according to claim 1, wherein the purge gas is configured to supply to the first sterilizer chamber and the second sterilizer chamber the purge gas at a pressure lower than or equal to atmospheric pressure.

6. A system according to claim 1, further comprising:
    a process gas analyzer coupled to at least one of the first sterilizer chamber and the second sterilizer chamber, the process gas analyzer configured to determine an amount of at least one of the sterilant gas mixture and the purge gas present in the combined mixture.

7. A system according to claim 6, wherein the sterilant gas mixture supply and the purge gas supply refortify the combined mixture with at least one of the sterilant gas mixture and the purge gas based on the determined amount in the combined mixture.

8. A system for recovery of a sterilant gas mixture comprising:
    a sterilant gas mixture supply including a sterilant gas mixture comprising ethylene oxide; and
    a first sterilizer chamber in gaseous communication with a second sterilizer chamber via a gas recovery assembly, wherein the first and second sterilizer chambers are coupled to the sterilant gas mixture supply and are configured to house at least one object for sterilization and the gas recovery assembly includes a vacuum pump and a circulation blower configured to transfer the sterilant gas mixture between the first sterilizer chamber and the second sterilizer chamber.

9. A system according to claim 8, further comprising:
    a purge gas supply coupled to at least one of the first sterilizer chamber and the second sterilizer chamber, the purge gas supply configured to supply a purge gas to at least one of the first sterilizer chamber and the second sterilizer chamber after the sterilant gas mixture is withdrawn, wherein the gas recovery assembly is configured to transfer the purge gas to form a combined mixture of the sterilant gas mixture and the purge gas.

10. A system according to claim 9, wherein the purge gas is an inert gas.

11. A system according to claim 9, further comprising:
    a process gas analyzer coupled to at least one the first sterilizer chamber and the second sterilizer chamber, the process gas analyzer configured to determine an amount of at least one of the sterilant gas mixture and the purge gas present in the combined mixture.

12. A system according to claim 11, wherein the sterilant gas mixture supply and the purge gas supply refortify the combined mixture with at least one of the sterilant gas mixture and the purge gas based on the determined amount in the combined mixture.

13. A system according to claim 8, wherein the gas recovery assembly is configured to evacuate at least one the first sterilizer chamber and the second sterilizer chamber prior to transferring the sterilant gas mixture thereto.

14. A system for recovery of a sterilant gas mixture comprising:
   a sterilant gas mixture supply including a sterilant gas mixture comprising ethylene oxide; and
   a plurality of sterilizer chambers, wherein each of the plurality of sterilizer chambers is in gaseous communication with at least one other sterilizer chamber and the sterilant gas mixture supply, wherein each of the plurality of sterilizer chambers is configured to house at least one object for sterilization; and
   a gas recovery assembly coupled to the plurality of sterilizer chambers, the gas recovery assembly includes a vacuum pump and a circulation blower configured to transfer the sterilant gas mixture present in one of the plurality of sterilizer chambers to at least one other sterilizer chamber.

15. A system according to claim 14, further comprising:
   a sterilant gas mixture supply coupled to the plurality of sterilizer chambers; and
   a purge gas supply coupled to the plurality of sterilizer chambers, the purge gas supply configured to supply a purge gas to the plurality of sterilizer chambers after the sterilant gas mixture is withdrawn from one of the plurality of sterilizer chambers to at least one other sterilizer chamber, wherein the gas recovery assembly is configured to transfer the purge gas to form a combined mixture of the sterilant gas mixture and the purge gas.

16. A system according to claim 15, wherein the purge gas is an inert gas.

17. A system according to claim 15, further comprising:
   a process gas analyzer coupled to the plurality of sterilizer chambers, the process gas analyzer configured to determine an amount of at least one of the sterilant gas mixture and the purge gas present in the combined mixture.

18. A system according to claim 17, wherein the sterilant gas mixture supply and the purge gas supply refortify the combined mixture with at least one of the sterilant gas mixture and the purge gas based on the determined amount in the combined mixture.

19. A system according to claim 14, wherein the gas recovery assembly is configured to evacuate one of the plurality of sterilizer chambers prior to transferring the sterilant gas mixture thereto.

* * * * *